United States Patent [19]

Hasegawa

[11] Patent Number: 4,807,598
[45] Date of Patent: Feb. 28, 1989

[54] ENDOSCOPE HAVING FIXING AND EXPANDING MEMBERS

[75] Inventor: Hiroshi Hasegawa, Hachioji, Japan

[73] Assignee: Olympus Optical Co., Ltd., Tokyo, Japan

[21] Appl. No.: 152,263

[22] Filed: Feb. 4, 1988

[30] Foreign Application Priority Data

Feb. 5, 1987 [JP] Japan .................. 62-025677

[51] Int. Cl.$^4$ ............................. A61B 1/06
[52] U.S. Cl. .................................... 128/6
[58] Field of Search ............... 128/4, 6; 138/120

[56] References Cited

U.S. PATENT DOCUMENTS

| 3,188,117 | 6/1965 | Press et al. | 128/120 X |
| 4,066,070 | 1/1978 | Utsugi | 128/4 |
| 4,085,742 | 4/1978 | Okada | 128/6 X |
| 4,224,929 | 9/1980 | Furihata | 128/6 X |

FOREIGN PATENT DOCUMENTS 57-37322  3/1982  Japan .

Primary Examiner—William H. Grieb
Attorney, Agent, or Firm—Armstrong, Nikaido, Marmelstein & Kubovcik

[57] ABSTRACT

An endoscope comprises an elongated insertable part, illumination device for illuminating an object to be imaged, and observing device for allowing observation of the object to imaged upon receiving a light from the object incident from an observing window disposed at a tip portion of the insertable part, the insertable part being provided with an inner tube and a tubular outer cover for covering the outer periphery of the inner tube. The outer cover is fixed to the inner tube by means of a cylindrical fixing member externally fitted to the outer cover. Further, a cylindrically projecting member for radially expanding the outer cover is provided in the vicinity of and on the outside of at least one axially opposite end portion of the fixing member in such a manner that an outside diameter of the outer cover in the vicinity of and on the outside of the axially opposite end portion of the fixing member becomes substantially equivalent to that of the fixing member.

17 Claims, 6 Drawing Sheets

4,807,598

ENDOSCOPE HAVING FIXING AND EXPANDING MEMBERS

BACKGROUND OF THE INVENTION

1. Field of the Invention

This invention relates to an endoscope wherein an insertable part is covered with a tubular outer cover.

2. Related Art Statement

In recent years, medical endoscopes are extensively used to observe organs within a body cavity by inserting an elongated insertable part into the body cavity or to make various curing treatments by using forceps inserted through a forceps channel as required. In the industrial field, industrial endoscopes are also extensively used to observe or inspect the interior of boilers, turbines, engines, chemical plants or the like.

A rigid tip part is provided on the tip side of the insertable part of the endoscope, and a curvable part is provided on the rear side adjacent to this tip part. The curvable part can be curved vertically and horizontally by rotating a curving operation knob provided on an operating part.

Among the industrial endoscopes, there is one in which the insertable part is protected by an outer protective sheath constituted by a net tube (blades) obtained by knitting fine wires of a metal or the like into the form of a net. In addition, there is another industrial endoscope in which the strength of the tightness of the outer protective sheath is varied between the curvable part and a flexible part disposed rearwardly of the curvable part because the degree of curvature varies between the curvable part and the flexible part. When the strength of the tightness of the outer protective sheath is thus to be varied, the outer protective sheath in the vicinity of a boundary between the curvable part and the flexible part is secured to an inner flexible pipe protected by the outer protective sheath, by means of a cylindrical fixing member externally fitted onto the outer protective sheath.

However, since the cylindrical fixing member projects radially outwardly of the outer periphery of the outer protective sheath, there is a problem in that particularly when the insertable part is removed from an object into which the insertable part is inserted, an end portion of the fixing member may be caught inside the object into which the insertable part is inserted.

OBJECT AND SUMMARY OF THE INVENTION

An object of the present invention is to provide an endoscope which is capable of preventing a cylindrical fixing member for fixing an outer cover of an insertable part from being caught in an object into which the insertable part is inserted.

To this end, in accordance with the present invention, there is provided an endoscope comprising: an elongated insertable part having an inner tube and a tubular outer cover for covering an outer peripheral part of the inner tube; illuminating means for illuminating an object; observing means having an observing window provided at a tip portion of the insertable part and adapted to allow observation of the object upon receiving a light from the object made incident from the observing window; a cylindrical fixing member fitted externally to the outer cover and adapted to fix the outer cover to the inner tube; and a cylindrically projecting portion which is disposed between the outer cover and the inner tube and in the vicinity of and on the outside of at least one axially opposite end portion of the fixing member and which is adapted to radially expand the outer cover in such a manner that an outside diameter of the outer cover in the vicinity of and on the outside of the axially opposite end portion of the fixing member becomes substantially identical with that of the fixing member.

Other features and advantages of the present invention will become apparent from the following detailed description of the invention.

BRIEF DESCRIPTION OF THE DRAWINGS

FIGS. 1 to 6 relate to a first embodiment of the present invention, in which

FIG. 1 is an enlarged cross-sectional view of a fixing member of a protective outer fitted sheath;

FIG. 2 is a cross-sectional view taken along the line C-C' of FIG. 4;

FIG. 3 is a cross-sectional view illustrating a tip portion of the insertable part in the vicinity of a light guide at a tip;

FIG. 4 is a view taken in the direction of an arrow A in FIG. 2;

FIG. 5 is a cross-sectional view taken along the line B-B' of FIG. 2;

FIG. 6 is a side elevational view of an overall endoscope;

DETAILED DESCRIPTION OF THE PREFERRED EMBODIMENTS

FIGS. 1 to 6 illustrate a first embodiment of the present invention.

Figure 6:
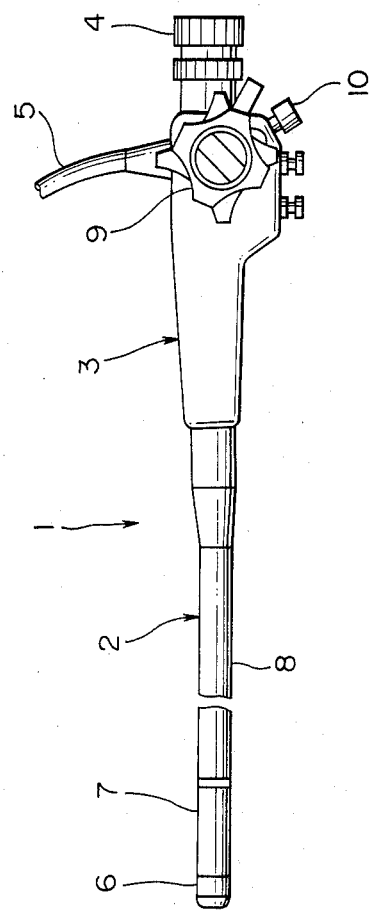

As shown in FIG. 6, an (industrial) endoscope 1 comprises an elongated insertable part 2, a large-diameter operating part 3 connected the rear end side of this insertable part 2, an eyepiece part 4 provided at the rear end of this operating part 3, and a light guide cable 5 extending from the side of the operating part 3.

A rigid tip part 6 is provided on the tip side of the insertable part 2, and a curvable part 7 is provided on the rear side adjacent to this tip part 6. A flexible part 8 is provided on the rear side of this curvable part 7. The curvable part 7 can be curved vertically and horizontally by rotating a curving operation knob 8 provided on the operating part 3. The operating part 3 is provided with an inserting port 10 which communicates with a treating tool channel provided within the insertable part 2.

The insertable part 2 is arranged as shown in FIGS. 1 to 5.

The tip part 6 is provided with a substantially columnar tip body 11 made of such a rigid material as a metal. In this tip body 11, there are formed an observing through hole 12, a treating tool channel through hole 13, and two illuminating through holes 14 all passing passing in parallel with the lengthwise direction of the insertable part 2.

An objective lens system 15 is fitted in the observing through hole 12. An image guide 16 of fibers high in flexibility is rrranged as an image transmitting means so as to have its tip surface positioned at a position in which an optical image of an object to be imaged is formed by this objective lens system 15. This image guide 16 of fibers is bundled on he tip side by a mouthpiece 17, is fitted to the observing through hole 12, is covered with a flexible tube 18, and is inserted through the insertable part 2 to transmit an optical image to the eyepiece part 4.

On the other hand, a treating tool channel mouthpiece 19 is fitted on the rear end side of the treating tool channel through hole 13, and a treating tool channel tube 21 forming the treating tool channel 20 is connected to the rear end of this treating tool channel mouthpiece 19. This treating tool channel tube 21 is inserted into the insertable part 2 and is connected to the inserting port 10 of the operating part 3.

Figure 3:
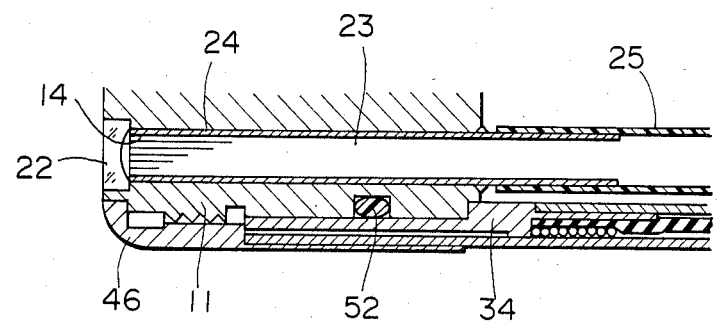
Figure 4:
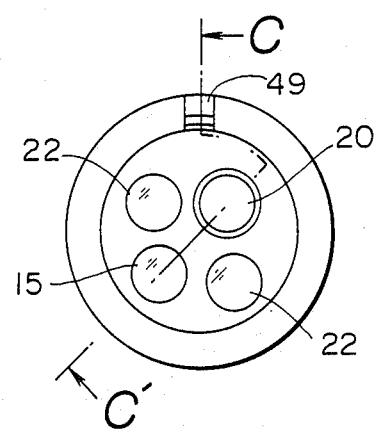

As shown in FIG. 3, a light distributing lens 22 is fitted to the tip part of the illuminating through hole 1 and has a light guide 23 of fibers connected to the rear end thereof. This light guide 23 of fibers is bundled on the tip side by a mouthpiece 24, is fitted to the illuminating through hole 14, is covered with a flexible tube 25, is inserted through the insertable part 2, and is connected to the light guide cable 5.

A multiplicity of substantially annular articulating frames 31 are rotatably connected in the longitudinal direction of the insertable part 2 within the curvable part 7 adjacent to the tip part 6. For example, four operating wires 32 inserted through the insertable part 2 and connected each at one end to the curving operation knob 9 are connected each at the other end to an articulating frame 31a at the foremost end. By pulling and relaxing the operating wires 32 by operating the curving operation knob 8, the curvable part 7 can be curved vertically and horizontally.

Figure 5:
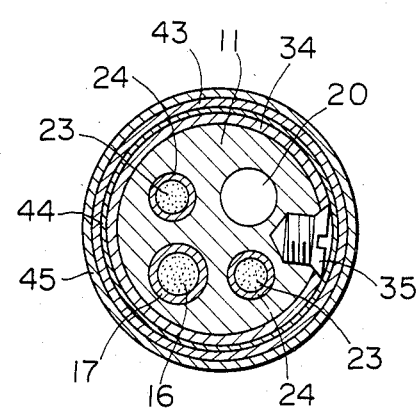

The articulating frame 31a at the foremost end is internally fitted and secured to the rear end of a cylinder 34. As shown in FIG. 5, this cylinder 34 is externally fitted to the tip body 11 and is fixed to the tip body 11 with a screw 35. An annular groove 51 is formed on the outer periphery of the tip body 11, and an O-ring 52 is fitted in this groove 51. The arrangement is such that the liquid-tightness between the cylinder 34 and the tip body 11, i.e., between the tip part 6 and the curvable part 7, can be maintained by this O-ring 52.

The articulating frame 31a is accommodated in an inner net tube (blade) 33 obtained by knitting fine wires of a metal or the like into the form of a net. The outer periphery of this inner net tube 33 is covered with a flexible tube 36 made of rubber or the like so as to be easy to curve. The tube 36 is bonded at both ends with a bonding agent, for example, after being wound with a thread so as to be fixed liquid-tightly.

The flexible part 8 is constituted by a net tube 39 and an inner flexible tube 40 formed of a resin or the like which covers the net tube 39. A flexible spiral tube 41 formed by spirally winding an elongated sheet-like member is housed on the inner periphery of the net tube 39. The image guide 16, light guide 23, treating tool channel tube 21, and the like are inserted through the interior. The net tube 39, inner flexible tube 40, and spiral tube 41 are connected to the articulating frame 31 at the rearmost end of the curvable part 6 by means of a mouthpiece 37. The mouthpiece 37 has a small-diameter cylindrical portion 37a and a large-diameter cylindrical portion 37b. The smaller-diameter cylindrical portion 37a is connected to the articulating frame 31, while forward end portions of the net tube 39, inner flexible tube 40, and the spiral tube 41 are internally fitted in the large-diameter cylindrical portion 37b.

The outer periphery of the inner flexible tube 40 constituting the tube 36, the mouthpiece 37, and the flexible part 8 in the curvable part 7 is covered with a protective outer fitted sheath 43 constituted by a net tube or the like obtained by knitting fine wires of a metal or the like into the form of a net. The front end portion of this protective outer fitted sheath 43 is clamped by an inner tube 44 and an outer tube 45. In this embodiment, a step 34a is formed peripherally on the outer periphery of the cylinder 34 externally fitted to the tip body 11, and the inner tube 44 is retained by this step 34a.

In addition, a substantially cylindrical cover member 46 is externally fitted and secured to the tip side of the tip body 11. A rear end portion of this cover member 46 is adapted to press the tip portions of the inner and outer tubes 44, 45 and the protective outer fitted sheath 43 clamped by the same, while the inner tube 44 is clamped by the cover member 46 and the step 34a of the cylinder 34 so as to fix the front side of the protective outer fitted sheath 43.

The cover member 46 is provided on the inner periphery thereof with an internal thread 47 on the inner periphery thereof to be screwed with an external thread provided on the outer periphery of the tip body 11, and is bonded with a bonding agent so as to be fixed to the tip body 11. Also, in this embodiment, the cover member 46 is provided with a slit 48 in the axial direction and further with a connecting part 49 connecting the slit 48 in the direction perpendicular to the axial direction. This connecting part 49 is formed to be thin so as to be able to be cut with a file or the like. When the protective outer fitted sheath 43 is removed for a repair or the like, the connecting part 49 connecting the slit 48 of the cover member 46 is cut by using a file or the like. Then, a screwdriver or the like is inserted into the slit 48 and the slit 48 is opened, thereby allowing the cover member 46 to be removed. Since the cylinder 34 at the tip part of the protective outer fitted sheath 43 clamped by the inner and outer tubes 44, 45 is disengaged from the step 34a, the protective outer fitted sheath 43 can be removed. Thus, according to this embodiment, since a screw or the like is not used to fix the protective outer fitted sheath 43, no screw or the like will drop during the inspection.

Figure 1:
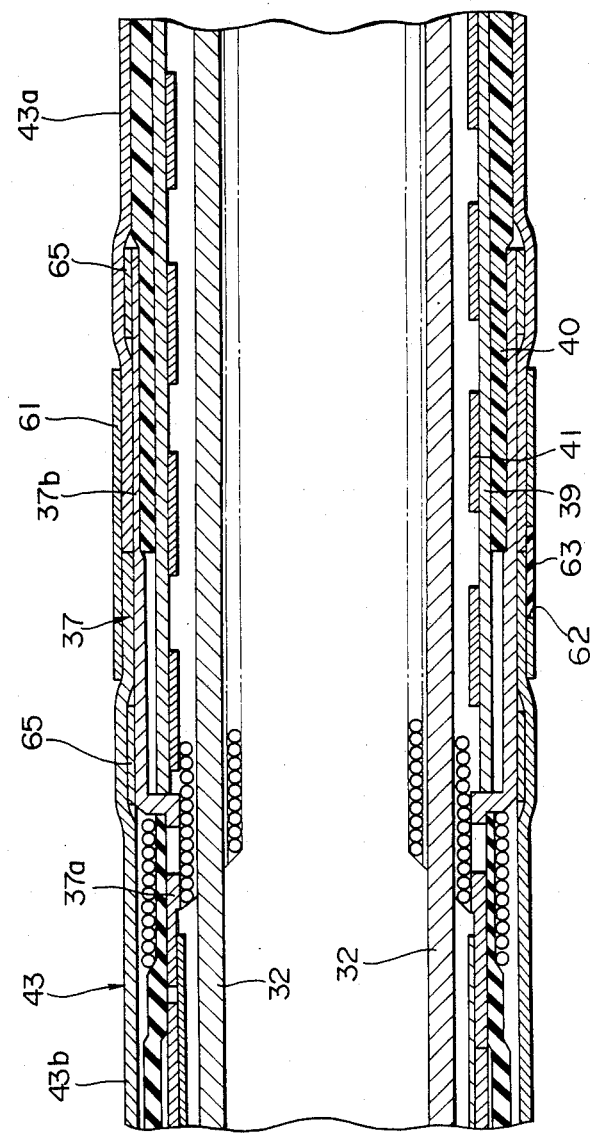
Figure 2:
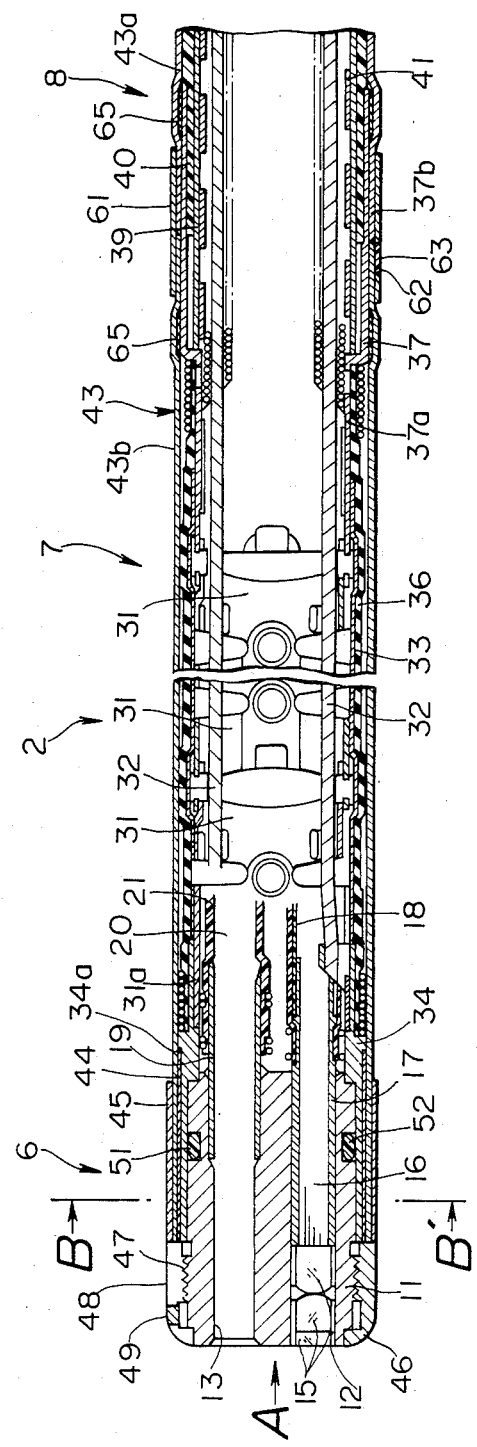

As shown in FIG. 1, the protective outer fitted sheath 43 comprises a flexible portion 43a on the side of the flexible part 8 and a curvable portion 43b on the side of the curvable part 7. The flexible portion 43a is impregnated with a resin to improve its durability, while the curvable portion 43b is not impregnated with a resin. A boundary between the flexible portion 43a and the curvable portion 43b is formed such as to be located substantially at a central portion of the large-diameter cylindrical portion 37b of the mouthpiece 37. The protective outer fitted sheath 43 is adjusted in such a manner that the flexible portion 43a is tight so as not to become lax, while the curvable portion 43b is less tight so as to maintain its favorable bending characteristics. The protective outer fitted sheath 43 is secured by a cylindrical fixing member 61 externally fitted to the protective outer fitted sheath 43. This fixing member 61 is arranged such that its axial length is shorter than that of the large-diameter cylindrical portion 37b of the mouthpiece 37, and is provided with a hole 62 for allowing an adhesive to flow thereinto. This fixing member 61 is arranged substantially in the center of the large-diameter cylindrical portion 37b of the mouthpiece 37 in such a manner as to cover the flexible portion 43a and curvable portion 43b of the protective outer fitted sheath 43. The fixing member 61, protective outer fitted sheath 43, and mouthpiece 37 are bonded to each other and fixed by an adhesive 63 poured into the hole 62.

In this embodiment, a pair of cylindrically projecting members 65 for radially expanding the protective outer fitted sheath 43 are respectively bonded and secured to the outer periphery of the large-diameter cylindrical portion 37b of the mouthpiece 37 and at positions adjacent and outside of the opposite end portions of the fixing member 61 in the axial direction thereof. The thickness of each of these projecting members 65 is formed to be substantially identical with that of the fixing member 61. By virtue of these projecting members 65, the protective outer fitted sheath 43 is expanded radially in the vicinity of and on the outside of the opposite end portions of the fixing member 61 in the axial direction thereof. Consequently, the outside diameter of these projecting portions becomes substantially identical with that of the fixing member 61, so that no step will be created between an end portion of the fixing member 61 and the protective outer fitted sheath 43.

The fixing member 61 is provided with a slit formed, for instance, in the axial direction. When the fixing member 61 is moved, for instance, from the tip side and is installed between the projecting portions 65, the arrangement is such that the fixing member 61 is adapted to slighly expand when it overrides the projecting portion 65.

Thus, in this embodiment, the pair of cylindrically projecting members 65 are respectively bonded and secured to the outer periphery of the large-diameter cylindrical portion 37b of the mouthpiece 37 and at positions adjacent to the outside of the opposite end portions of the fixing member 61 in the axial direction thereof. By virtue of these projecting members 65, the protective outer fitted sheath 43 is expanded radially in the vicinity of and on the outside of the opposite end portions of the fixing member 61 in the axial direction thereof. Consequently, the outside diameter of these projecting portions becomes substantially identical with that of the fixing member 61, so that no step will be created between an end portion of the fixing member 61 and the protective outer fitted sheath 43. Accordingly, when the insertable part 2 is inserted into an object and when the insertable part 2 is removed from the object, the end portions of the fixing member 61 will not be caught inside the object.

Figure 7:
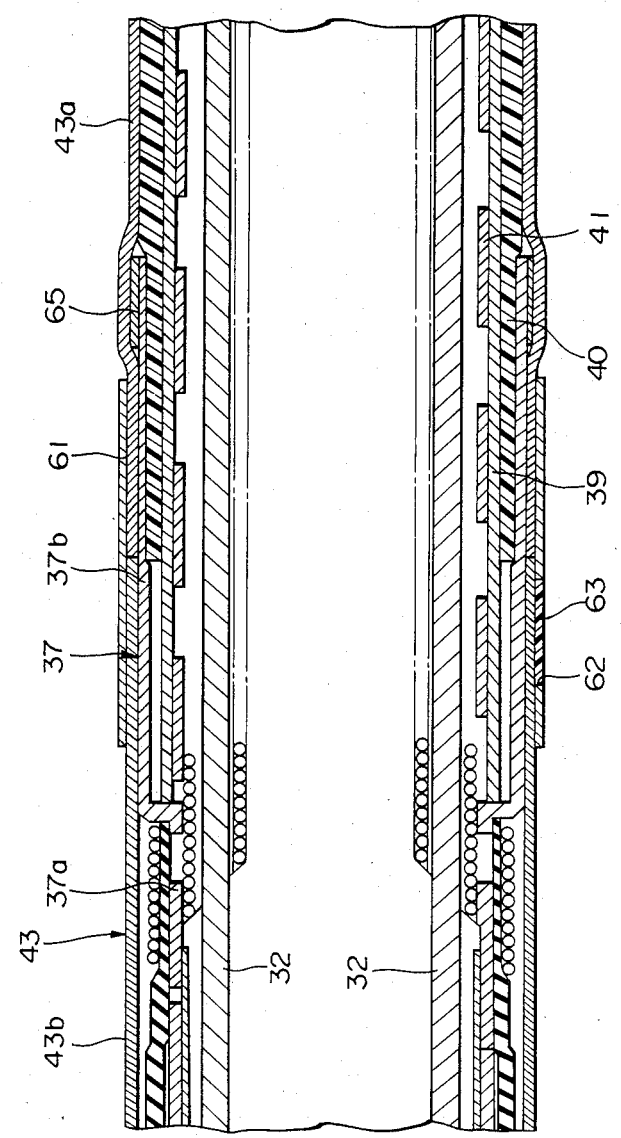
FIG. 7 an an enlarged cross-sectional view of a fixing part of the protective outer fitted sheath of the endoscope in accordance with a second embodiment of the present invention.

FIG. 7 shows a second embodiment of the present invention.

In this embodiment, the cylindrically projecting portion 65 is provided only on the rear end side of the fixing member 61. The other arrangements are the same as those of the first embodiment.

When the insertable part 2 is removed from the object, there is a possibility that, if the fixing member 61 is caught inside the object, the insertable part 2 cannot be removed from the object. Since this catching of the fixing member 61 at the time of removal presents a greater problem than at the time of insertion, in this embodiment, it is possible to prevent the fixing member 61 from being caught at the time of the removal.

Incidentally, in accordance with this embodiment, there is no need to provide the fixing member 61 with the slit. When this fixing member 61 is installed, the fixing member 61 may be moved from the tip side to the side of the operating part 3 and fixed at a position at which its further movement is prevented by the projecting member 65.

The other operation and advantages of this embodiment are the same as those of the first embodiment.

Figure 8:
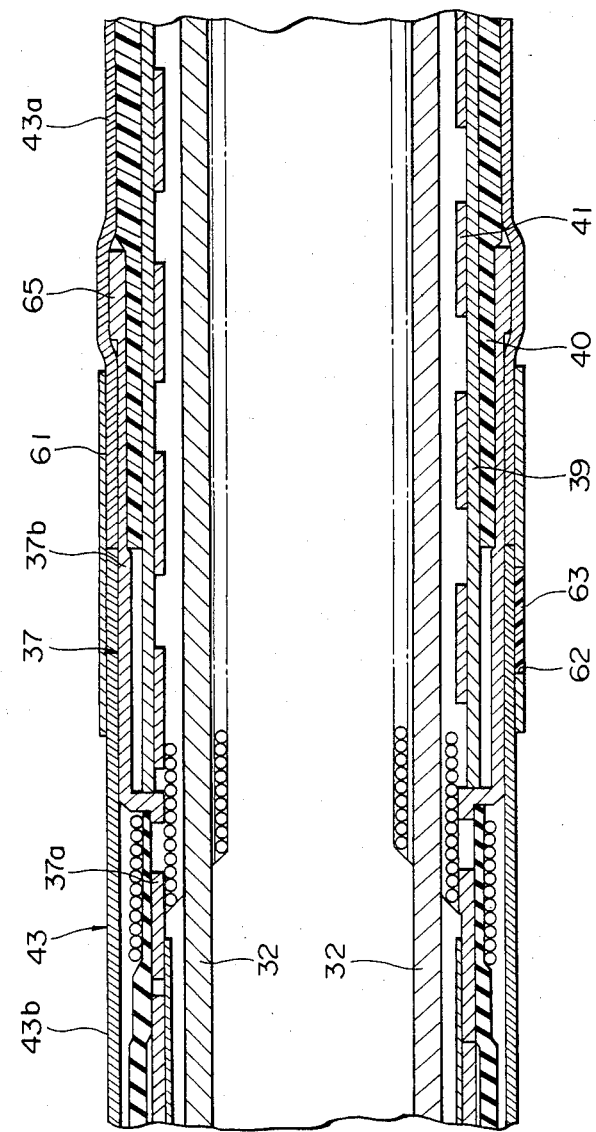
FIG. 8 is an enlarged cross-sectional view of the fixing part of the outer protective sheath of the endoscope in accordance with a third embodiment of the present invention.

FIG. 8 shows a third embodiment of the present invention.

In this embodiment, the cylindrically projecting member 65 is formed integrally with the mouthpiece 37 only on the rear end side of the fixing member 61. The other arrangements are the same as those of the second embodiment.

In accordance with this embodiment, it is possible to eliminate the operation of bonding the projecting member 65 to the mouthpiece 37, which is required in the first and second embodiments.

The other operation and advantages of this embodiment are the same as those of the second embodiment.

Incidentally, the cylindrically projecting members 65 may be formed integrally with the mouthpiece 37 respectively on the outside of the front and rear ends of the fixing member 61, in the same way as the first embodiment.

It should be noted that the present invention is not restricted to the foregoing embodiments, and, for instance, may be arranged such that the projecting member 65 is secured to the inner peripheral surface of the protective outer sheath 43.

In addition, an arrangement may be alternately provided such that the fixing member 61 is formed of a shape memory alloy, a super-resilient alloy, or a metal or the like having a large coefficient of thermal expansion and is, after being externally fitted to the protective outer fitted sheath 43, caused to shrink so as to be secured.

As has been described above, in accordance with the present invention, a cylindrically projecting portion for radially expanding an outer cover is provided between the outer cover and an inner tube covered with the outer cover and in the vicinity of and on the outside of at least one axially opposite end portion of a cylindrical fixing member for fixing the outer cover, in such a manner that an outside diameter of the outer cover in the vicinity of and on the outside of the axially opposite end portion of the fixing member becomes substantially equivalent to that of the fixing member. Accordingly, no step is created between an end portion of the fixing member and the outer cover, so that there is an advantage in that the fixing member is not caught in an object into which an insertable part is inserted.

In this invention, it is apparent that a wide range of working modes can be formed on the basis of this invention without deviating from the spirit and scope of the invention. This invention is not restricted to the specified working modes, except as limited by the appended claims.

What is claimed is:

1. An endoscope comprising:
   an elongated insertable part having an inner tube and a tubular outer cover for covering an outer peripheral part of said inner tube;
   illuminating means for illuminating an object;
   observing means having an observing window provided at a tip portion of said insertable part and adapted to allow observation of said object upon receiving a light from said object made incident from said observing window;

a cylindrical fixing member fitted externally to said outer cover and adapted to fix said outer cover to said inner tube; and a cylindrically projecting portion which is disposed between said outer cover and said inner tube and in the vicinity of and on the outside of at least one axially opposite end portion of said fixing member and which is adapted to radially expand said outer cover in such a manner that an outside diameter of said outer cover in the vicinity of and on the outside of said axially opposite end portion of said fixing member becomes substantially identical with that of said fixing member.

2. An endoscope comprising:

a flexible, elongated insertable part having an inner tube and a flexible, tubular outer cover for covering an outer peripheral part of said inner tube, said insertable part having a curvable portion provided on the tip side thereof and a flexible portion provided on the rear side of said curvable portion, said outer cover having a curvable portion corresponding to said curvable part and a flexible portion corresponding to said flexible part;

illuminating means for illuminating an object;

observing means having an observing window provided at a tip portion of said insertable part and adapted to allow observation of said object upon receiving a light from said object made incident from said observing window;

a cylindrical fixing member externally fitted and fixed to said outer cover in the vicinity of a boundary between said curvable portion and said flexible portion of said outer cover and adapted to fix said outer cover to said inner tube; and a cylindrically projecting portion which is disposed between said outer cover and said inner tube and in the vicinity of and on the outside of at least one axially opposite end portion of said fixing member and which is adapted to radially expand said outer cover in such a manner that an outside diameter of said outer cover in the vicinity of and on the outside of said axially opposite end portion of said fixing member becomes substantially identical with that of said fixing member so as to ensure that a step will not be created between said end portion of said fixing member and said outer cover.

3. An endoscope according to claim 1 or 2, wherein said outer cover is comprised of a net tube obtained by knitting fine wires of a metal into the form of a net.

4. An endoscope according to claim 1 or 2, wherein said fixing member has a hole penetrating inner and outer peripheral sides thereof and secured to said inner tube by means of an bonding agent poured into said hole.

5. An endoscope according to claim 1 or 2, wherein said curvable part of said insertable part has a plurality of substantially annular articulating frames connected to each other in the longitudinal direction thereof.

6. An endoscope according to claim 5, wherein said insertable part has a substantially cylindrical mouthpiece for connecting a rearmost articulating frame of said curvable part and a flexible tube constituting said inner tube in said flexible part, while said fixing member is disposed on an outer periphery of said mouthpiece to fix said outer cover to said mouthpiece.

7. An endoscope according to claim 6, wherein said projecting member is formed by a cylindrical member secured to said outer periphery of said mouthpiece.

8. An endoscope according to claim 7, wherein said cylindrical member forming said projecting member is disposed in the vicinity of and on the outside of each axially opposite end portion of said fixing member.

9. An endoscope according to claim 7, wherein said cylindrical member forming said projecting member is disposed only on the rear end side of a rear end portion of said fixing member.

10. An endoscope according to claim 6, wherein said projecting member is formed integrally with an outer peripheral portion of said mouthpiece.

11. An endoscope according to claim 10, wherein said projecting member is formed in the vicinity of and on the outside of each axially opposite end portion of said fixing member.

12. An endoscope according to claim 10, wherein said projecting member is formed only on the rear end side of a rear end portion of said fixing member.

13. An endoscope according to claim 2, wherein said outer cover is comprised of a net tube obtained by knitting fine wires of a metal into the form of a net, and said flexible portion of said outer cover is impregnated with a resin.

14. An endoscope according to claim 2, wherein said curvable portion of said outer cover is less tight than said flexible portion of said outer cover.

15. An endoscope according to claim 1 or 2, wherein said observing means comprises an objective lens system for imaging a light returning from said object and incident from said observing window, an eyepiece part provided in an operating part connected to a rear end of said insertable part, and an image guide of fibers inserted through said insertable part, having a tip surface thereof disposed at an image-forming position of said objective lens system, and leading an image formed by said objective lens system to said eyepiece part.

16. An endoscope according to claim 1 or 2, wherein said illuminating means is provided with an illuminating window disposed at a tip portion of said insertable part and a light guide of fibers inserted through said insertable part and leading an illuminating light from a light source to said illuminating window.

17. An endoscope according to claim 1 or 2, further comprising a treating tool channel formed in said insertable part.

* * * * *